United States Patent [19]

Haritonidis et al.

[11] Patent Number: 4,896,098
[45] Date of Patent: Jan. 23, 1990

[54] TURBULENT SHEAR FORCE MICROSENSOR

[75] Inventors: Joseph H. Haritonidis, Cambridge; Roger T. Howe, Belmont; Martin A. Schmidt, Brookline; Stephen D. Senturia, Boston, all of Mass.

[73] Assignee: Massachusetts Institute of Technology, Cambridge, Mass.

[21] Appl. No.: 273,106

[22] Filed: Nov. 16, 1988

Related U.S. Application Data

[63] Continuation-in-part of Ser. No. 1,824, Jan. 8, 1987, abandoned.

[51] Int. Cl.$^4$ .............................................. G01R 27/26
[52] U.S. Cl. ..................................... 324/663; 361/285
[58] Field of Search ...................... 73/432.1, 760, 767, 73/774, 777, 780, 800, 862, 862.62–862.69; 361/280, 285; 324/61 R

[56] References Cited

U.S. PATENT DOCUMENTS

| | | | |
|---|---|---|---|
| 3,462,223 | 8/1969 | Tiemann et al. | 73/800 |
| 3,641,812 | 2/1972 | Vick | 73/767 |
| 3,714,824 | 2/1973 | Bush . | |
| 4,141,252 | 2/1979 | Lodge | 73/724 |
| 4,423,371 | 12/1983 | Senturia et al. | 324/61 R |
| 4,451,780 | 5/1984 | Ogasawara | 324/61 R |
| 4,475,392 | 10/1984 | Ajagu et al. . | |
| 4,543,526 | 9/1985 | Burckhardt et al. | 324/61 R |
| 4,592,238 | 6/1986 | Busta . | |
| 4,703,663 | 11/1987 | Oppermann | 73/862.63 |
| 4,744,863 | 5/1988 | Guckel et al. . | |
| 4,783,821 | 11/1988 | Muller et al. . | |
| 4,816,125 | 3/1989 | Muller et al. . | |

FOREIGN PATENT DOCUMENTS

1470591 4/1977 United Kingdom .................. 73/780

OTHER PUBLICATIONS

"Measurement of Wall Shear Stress", T. J. Hanratty and J. A. Campbell Fluid Mechanics Measurements, R. J. Goldstein (Editor), Hemisphere Publ. Corp., 1983, pp. 559–615.
"An Outline of the Techniques Available for the Measurement of Skin Friction in Turbulent Boundary Layers", K. G. Winter, Prog. Aerospace Sci. 1977, vol. 18, pp. 1–57, Pergamon Press.

(List continued on next page.)

Primary Examiner—Robert R. Raevis
Attorney, Agent, or Firm—Hamilton, Brook, Smith & Reynolds

[57] ABSTRACT

A microbridge is used for the accurate measuring of time varying shear forces in the presence of fluctuating pressure. A microdimensioned plate is suspended by arms to form a microbridge. The microdimensions enable the smallest turbulence scales of interest to be sensed uniformally throughout the entire surface of the plate. The cavity beneath the microbridge is so small that a viscous drag is created in the air within the cavity and dampens normal movement of the plate. The microdimensions in conjunction with the damping effect of the cavity enable the sensor to be substantially insensitive to pressure and thus sense lateral forces independent of normal forces. The microbridge sensor is fabricated by surface micromachining. A sacrificial layer is deposited over a substrate. A structural layer is deposited and patterned to form the plate and support arms over the sacrificial layer. The cavity is formed by a selective etchant removing the sacrificial layer and leaving the rest of the microbridge structure suspended above the substrate. In a differential capacitance readout scheme, a conducting layer in the plate of the microbridge is capacitively coupled with conductors in the substrate. A sensed change in capacitive coupling generates an indication of plate deflection and thereby shear stress independent of vertical movement. Optic readout schemes may also be employed and are readily incorporated in the fabrication process. A mounting member presses the microbridge sensor into a holding plate which fits in a matching slot flush with the target wall.

54 Claims, 9 Drawing Sheets

OTHER PUBLICATIONS

"Improved Sensing Element for Skin-Friction Balance Measurements", J. M. Allen, AIAA Journal, vol. 18, No. 11, Article No. 80-0049R, pp. 1342-1345.

"Application of the Force-Balance Principle to Pressure and Skin Friction Sensors", J. M. Paros, 1970 Proceedings, Inst. of Enviromental Sciences, 16th Annual Tech Mtg., Apr. 12-16, 1970, Boston, MA, pp. 363-368.

"Direct Measurements of Skin Friction in a Turbulent Boundary Layer with a Strong Adverse Pressure Gradient", D. Frei and H. Thomann, *J. Fluid Mech.* (1980), vol. 101, Part 1, pp. 79-95, Cambridge University Press.

"The instrumentation of a modern fluid mechanics research laboratory", M. P. Escudier, *Measurement and Control*, vol. 6, No. 7, Jul. 1983, (Dorking, GB), pp. 267-271.

"A servo force-balance instrument for the direct measurement of wall shear stress on circular cylinders", D. B. Macvean et al., *J. Physics E: Sci. Instrum.*, vol. 11, No. 10, Oct. 1978, The Institute of Physics, pp. 1048-1050.

"Resonant-Microbridge Vapor Sensor", Howe, et al., *IEEE, Transactions on Electron Devices,* vol. ED-33, No. 4, Apr. 1986, IEEE, (New York, US), pp. 499-505.

"Integrated silicon PI-FET accelerometer with proof mass":, P. L. Chen, et al., *Sensors and Actuators,* vol. 5, No. 2, Feb. 1984, Elsevier Sequoia, (Lausanne, CH), pp. 119-126.

"Silicon sensors meet integrated circuits", Philip W. Barth, *IEEE Spectrum, vol. 18, No. 9, Sep. 1981, IEEE, (New York, US), pp. 33-39.*

TURBULENT SHEAR FORCE MICROSENSOR

This is a continuation-in-part of co-pending application Ser. No. 001,824 filed on Jan. 8, 1987, now abandoned.

DESCRIPTION

1. Background of the Invention

The wall shear stress is one of the most important parameters in studying bounded turbulent flows. Both the mean and the fluctuating part of the shear stress are manifestations of the overall structure of the flow above the wall. The mean value determines the drag characteristics of a particular configuration, while the fluctuating part is of importance in sound generation, separated flows, passive or active control of turbulence and, in general, assessment of which types of flow structures are primarily responsible for momentum transfer between the outer part of the boundary layer and the wall.

A number of investigations have concentrated on the near-wall structure of turbulence, mostly in channel, pipe and planar boundary-layer flows. Measurements to date show a rather large scatter in measured values of the shear stress, in many instances, using the same probes under almost identical conditions. The measurements of the fluctuating shear stress cover a range whose extreme values differ by approximately an order of magnitude. It is therefore clear that the measurement of the fluctuating shear stress is not a trivial matter and, furthermore, the correct value is not known with any certainty.

One of the most common methods used to measure shear stress is a pressure sensing tube, such as the Preston tube. The pressure sensed by the Preston tube is a function of the non-dimensional velocity profile. The velocity profile is rendured non-dimensional using the wall shear stress. Thus, the measured pressure can be directly related to the wall shear stress. This method, however, depends on knowledge of the velocity profile which can be assumed known only in a limited number of cases. Furthermore, the Preston tube is not suitable for the measurements of fluctuating shear stress.

Other methods typically employ flush-mounted hot-films in both gases and liquids where a heated strip with a temperature greater than the ambient is placed along the sample wall. The heat loss from the strip is measured and can be related to the shear stress at the wall because greater fluid velocity creates greater heat loss from the surface. With proper calibration of this temperature-velocity relationship, shear stress measurements are obtained. However, the heat from the strip often causes a change in surface and fluid temperature thereby causing inaccuracies in measurement and calibration. In one example, the wall region was investigated in three different facilities using hot wires, hot films, flush mounted films, and flush mounted hot wires. The conclusion was that most of the discrepancies between investigators using hot films were attributed to either improper calibration and/or different film substrates. Hence, there is a distinct disadvantage in using films in that their characteristics are extremely sensitive to the substrate material and its temperature. In addition, the signal-to-noise ratio is rather small compared to ordinary hot wires, and the output is nonlinear. As a result, their use is cumbersome and unreliable, particularly when quantitative measurements are desired. Also, hot wire techniques are limited in application.

Electrochemical and photochemical techniques have also been used, but with no obvious advantages.

Floating element shear stress sensors have also been used to measure wall shear. Such sensors include a plate positioned in an opening in the sample wall and supported on a pedestal. An electric coil or a weight is used to reposition the shearing plate to equilibrium. The current in the coil or the force of the weight used in recentering the plate serves as a measurement of the amount of average shear stress experienced by the element. However, this method usually does not allow for the measuring of fluctuating shear stress, and only measures relatively large shear stress forces. Further disadvantages in this approach have been problems with pressure gradient across the floating element, fluid flow through the gap area which produces apparent and erroneous forces, communication with ambient due to the large gap, and scale resolution.

Other methods only measure forces in an air fluid or a water fluid but not both. Some methods are dependent on gravity and thus, only work on a horizontal target surface. Further, most methods are hard to install, may disturb the flow of the fluid, and are expensive.

2. Summary of the Invention

In bounded turbulent flow, lateral forces generate a shear stress on the boundary wall. In measuring the wall shear stress, there is a mean component and a fluctuating component. Further, non-lateral fluctuating forces, such as environmental pressures and eddies, affect the measuring of wall shear. It is thus desirable to provide a shear stress sensor that measures time varying shear in the presence of fluctuating pressure.

In accordance with the present invention, there is provided an extremely small shear stress sensor which substantially reduces the problems of pressure gradient across the floating sensor, gap flow and scale resolution of the prior art. The sensor also enables the resolving of very small turbulent scales.

The invention comprises a very small plate suspended above a substrate by arms or tethers to form a microbridge. The plate is considered to be micro-dimensioned which means that the most convenient unit of measurement is micrometers ($\mu$m) or microns. Such small dimensions render the plate substantially unresponsive to pressure and thus without appreciable vertical movement. In order for the plate to move vertically an appreciable amount, a pressure difference must be generated vertically between the pressure on top of the plate and that below the plate. Pressure differences may also occur laterally between various points across the top of the plate. Because the plate is microdimensioned, pressure differences between different points on the plate only occur at very high frequencies on the order of about one megahertz. Stated another way, pressure differences will not substantially move the plate unless, compared to the dimensions of the plate, the scale of the pressure difference is very small, such as those of turbulent fluctuations at high speeds. More specifically, in turbulent flow, a vertical pressure gradient will not cause substantial vertical movement of the plate provided the scale of the pressure fluctuation due to turbulent eddies is of the same order of magnitude or larger than the thickness of the plate. Likewise, lateral pressure gradients will not cause substantial vertical movement of the plate provided that the scale of pressure fluctuation of turbulent eddies is of the same order of magnitude or larger than the lateral dimension of the plate. What is meant by the phrase "scale of the pressure fluctuation" is the region in which the pressure is uniform. Hence, due to the very small lateral dimension and the thinness of the plate, the pressure distribution over the plate, both laterally and vertically, is substantially uniform such that the microbridge will not respond with any appreciable vertical movement.

Further, the plate is suspended at a height which forms a very small passageway or cavity beneath the microbridge. The dimensions of the passageway are so small that movement of the plate by forces due to vibration is heavily damped by a viscous damping within the passageway.

The dimensions of the plate and the damping effect of the passageway enable the microbridge to be substantially insensitive to normal forces yet very sensitive to shear forces acting on it. Readout means which are also insensitive to vertical movement are incorporated in the microbridge structure to provide an indication of sensed shear stress. The microbridge sensor thus enables lateral deflection of the plate indicative of shear stress to be sensed independent of pressure fluctuations.

In the preferred embodiment, a conducting layer is associated with the plate. The conducting layer is part of an integrated differential capacitance measuring circuit which produces the sensor readout. The conducting layer is capacitively coupled with three electrodes attached to the substrate. Two sense electrodes sense the capacitive coupling at each end of the conducting layer. The third electrode attached to the substrate is connected to an AC generator to produce a constant drive signal. Lateral deflection of the plate changes the capacitive coupling between drive and the sense electrodes. The coupling is decreased for one sense electrode and increased for the other. This offset is sensed by connected ammeters which produce an indication of the deflection and thereby a measurement of the sensed shear stress.

In another embodiment an optical readout scheme is employed. Distinguishing optical features are attached to the plate and are visible through a window in the substrate. Deflection of the plate and shear stress is then measured as a function of the movement of the optical features. Further, a scale may be associated with the substrate. Movement of the optical features is measured relative to the scale to provide an indication of sensed shear stress.

The microbridge structure is micro-fabricated utilizing two thin films on a substrate. The first film is a sacrificial layer deposited directly over the substrate. The second film is deposited over the sacrificial layer. The second film is patterned to form the plate and suspension arms which are attached to the substrate. The thin film layers are exposed to an etchant which removes only the sacrificial layer. The plate, arms and substrate remain forming a microbridge over a small cavity where the sacrificial layer was positioned.

The integrated circuit or other readout means is readily incorporated into the micro-fabrication process by surface micromachining and passivation which does not affect the material so the circuit or other readout means.

The microbridge structure may also be fabricated within a recess of the substrate. A sacrificial layer is deposited into a recess of the substrate. The second film is deposited over the sacrificial layer and is patterned to form the plate and arms. The sacrificial layer is removed leaving the microbridge suspended within the recess. The top surface of the plate is smooth with the substrate. A small cavity is formed between the plate and base of the recess where the sacrificial layer was previous to removal.

An alternative design which minimizes vertical and lateral perturbation of the microbridge into the flow is similar to the general micro-fabrication method. The first and second films are deposited and patterned in the same manner as in the general fabrication method. The second film, however, is also deposited over the rest of the substrate surface. The second film is planarized so that the thickness of the arms is greater than the thickness of the cavity and the plate protrudes above the rest of the film on the substrate by about the same distance as the cavity is thick or less.

Mounting means for the microbridge sensor position the readout means downstream from the microbridge so as to not disturb the flow before detection. The mounting means hold the microbridge sensor in a holding plate which fits into a matching slot in the target wall. The sensor is pressed by a jig piece to lie flush with the target wall within the holding plate.

BRIEF DESCRIPTION OF THE DRAWINGS

The foregoing and other objects, features, and advantages of the invention will be apparent in the following more particular description of the preferred embodiments of the invention, as illustrated in the accompanying drawings, in which like reference characters refer to the same parts throughout the different views. The drawings are not necessarily to scale, emphasis instead being placed upon illustrating the principles of the invention.

FIGS. 13a–13c are a plan view and crosssections of the microstructure of FIG. 2 used for sensing acceleration.

FIG. 14 is a graphical illustration of measured acceleration sensitivity of the microstructure of FIGS. 13a–13c.

DETAILED DESCRIPTION OF THE INVENTION

When a fluid flows over a solid boundary, the solid experiences a fluctuating shear stress. The fluid may be described as having two types of flow, a laminar flow and a turbulent flow. The laminar flow is a smooth, continuous, undisturbed flow. The turbulent flow is unsteady and contains eddies of different sizes. Additional shear forces are produced at the boundary wall due to these eddies. Depending upon the direction and magnitude of the additional forces, higher or lower resulting shear forces are formed at the wall. Hence, shear force in laminar flow is steady, and shear force measurements in turbulent flow is time dependent. It is also known that the fluid velocity is zero at the boundary wall. In laminar flow the fluid velocity increases in a linear fashion as a function of distance away from the wall. In turbulent flow the fluid velocity gradient within the turbulent boundary layer is faster than that of laminar flow. At the same free stream velocity of a laminar flow, a higher shear force exists close to the boundary wall in turbulent flow than in the laminar flow. It is the change in time of this shear force in turbulent flow which is of particular interest.

The present invention is directed toward but not limited to measuring time-varying shear force in turbulent flow. Other applications of the present invention include the measuring of average shear force. Further, the present invention enables an increased spatial resolution because the size of the shearable plate is smaller than any eddy to be resolved.

Figure 1:
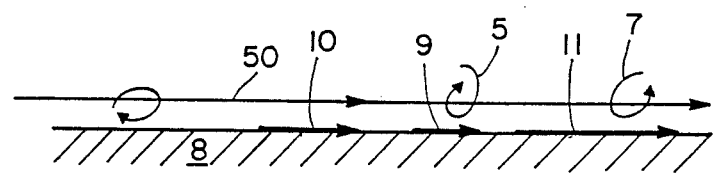
FIG. 1 is an illustration of turbulent flow over a bounded area.

FIG. 1 illustrates the time varying shear stress measured by the present invention. Fluid flow 50 in one direction produces a shear stress 10 in that same direction along wall 8. Eddy current 5 is shown flowing against fluid flow 50 and results in a shear stress 9 which is smaller than, but in the same direction as, shear stress 10. It is possible for the magnitude of an eddy, like eddy 5, to be larger than fluid flow 50 which would then result in a shear stress in the opposite direction (not shown). Also an eddy 7 may flow in the same direction as fluid flow 50. This results in a shear stress 11 which is larger than shear stress 9 or 10. This change in magnitude from shear stress 10 to 9 to 11 is the type of time varying wall-shear stress in turbulent flow that the present invention is capable of measuring and which has previously been unobtainable or inaccurately obtained by prior art means.

The present invention measures time varying shear stress through an element which is sensitive to the smallest eddies of the interest yet insensitive to nonlateral forces such as pressure. This is accomplished by suspending the element above a substrate such that the element is vertically balanced with no net pressure difference between pressures on top and those beneath the element, and by dimensioning the element so small that in order to generate a pressure difference, the pressure fluctuation must be at or above a very high frequency known as the cut-off frequency. Such dimensioning is made possible by micromachining techniques. These techniques involve deposition of thin films on a silicon wafer, and chemical etching of the film to shape and size. Further, the passageway or cavity formed beneath the element is of dimensions in which air or other gas becomes viscous and dampens vertical movement of the element. Readout schemes which are insensitive to vertical movement of the element are readily incorporated into the micromachining process to provide an indication of the sensed shear stress.

Figure 2:
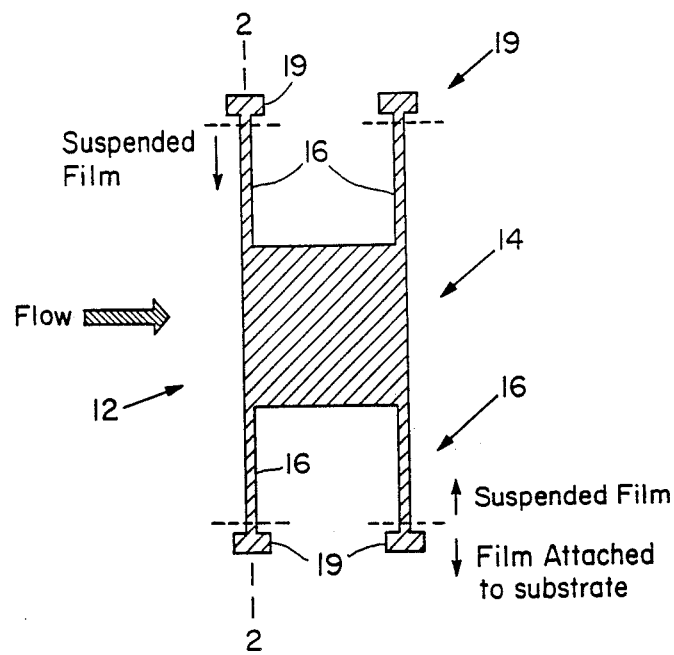
FIG. 2 is a plan view of a microbridge shear-sensitive element embodying the present invention.
Figure 3:
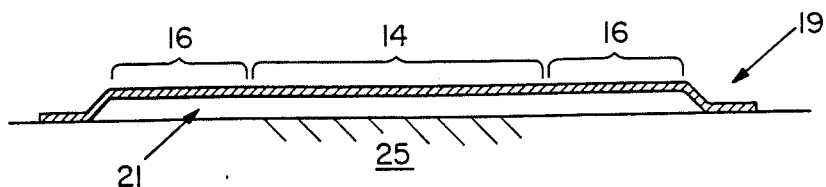
FIG. 3 is a cross section of the element of FIG. 2 through line 2—2.

A microbridge shear-sensitive element embodying the present invention is shown in FIGS. 2 and 3. The element 12 includes a thin film plate 14 having a width and length (Lp) of about 200 microns. Plate 14 is about 2 microns thick. Plate 14 is suspended less than about 3 microns above substrate 25 by four support arms 16. The ends of each arm 16 are attached to substrate 25 by four respective bases 19. Wall shear perpendicular to the support arms 16 causes plate 14 to deflect laterally which is observed through readout means, described later.

A passageway or cavity 21 is formed between suspended plate 14 and substrate 25. The pressure of the fluid experienced through the cavity is about the same as the pressure of the fluid across the top of the plate. Hence, plate 14 is in general vertically balanced. Where pressure of the fluid varies laterally across the plate, it does so in the same manner above and below the plate 14. Thus, the plate 14 remains vertically balanced.

Further at such small dimensions of cavity 21, viscous effects become important. Movement of the fluid in the cavity is limited due to viscous effects thus providing a viscous damping force on the plate. A gel may be inserted into the cavity to produce similar viscous effects in submersible applications of the invention or applications in a vacuum. Such a viscous force dampens movement of the plate 15 normal to the substrate and enables microbridge element 12 to sense shear force independent of non-lateral forces.

All non-lateral effects, such as pressure effects, are substantially eliminated by the micro-dimensions of element 12. More specifically, as long as the wavelengths of acoustical pressures are much larger than any characteristic dimension of thin-film plate 14, the plate will experience no appreciable net pressure difference between pressures on top and bottom or between opposite sides of the plate. Hence, the plate experiences a uniform pressure across its surfaces. Further, a wavelength of order Lp, the width and length of plate 14, corresponds to a pressure frequency f equal to 340/Lp Hz. For a typical Lp of 200 $\mu$m, f equals 1.7 MHz which is well above any acoustical frequency expected. For smaller Lp on the order of about 30 $\mu$m, f would be even more above any expected acoustical frequency. Thus the micro-dimensions of plate 14 enable the plate to be substantially insensitive to any acoustical pressures, thereby detecting shear forces free of pressure (non-lateral) effects.

There are also pressures generated locally by the turbulent flow field that must be considered. As with acoustical pressures, if the scale of the pressure fluctuation is large compared to Lp, then the plate 14 will experience a uniform pressure over its entire surface and substantially no effect will result. One of the smallest scales of pressure involved is of the order of 100 $L^*$ where $L^* = \nu/u^*$ and where $\nu$ is the fluid kinematic viscosity and $u^*$ is the friction velocity defined by $\tau u^{*2} = \tau$. $\rho$ is density and $\tau$ is shear stress. For high Reynolds number flows, say, over a flat smooth surface $u^* \approx 0.03\, U_\infty$ where $U_\infty$ is the free stream velocity. Taking a maximum $U_\infty = 20$ m/sec in air, give a $L^* = 25$ $\mu$m and a smallest scale of the order of 2,500 $\mu$m.

The dimensions of element 12 are an order of magnitude smaller than this smallest scale so that plate 14 experiences no effect from this type of pressure fluctuation.

Knowing that $u^* \approx 0.03\, U_\infty$ to $0.05\, U_\infty$, it is understood that the above stated numerical lengths are by way of illustration of the invention and not limitation. In general, the dimensions of the present invention may best be understood in terms of the characteristic length scale $L^*$. The relevant length scale in turbulent flow is $L^* = \nu/u^*$
where kinematic viscosity $\nu = \mu/\rho$
and friction velocity $$u^* = \sqrt{\frac{\tau}{\rho}}$$

$\tau$ is shear stress, $\rho$ is density, and $\mu$ is absolute viscosity of the fluid. In accordance with the foregoing details of the present invention, it follows that the height of the microbridge 12 above substrate 25 or the total protrusion of the microbridge 12 from the target surface is no more than about $2L^*$ to about $3L^*$, and the longitudinal or lateral dimension, Lp, is no larger than about $5L^*$ to about $10L^*$.

Given that the microsensor element 12 has dimensions so small that it responds to wall shear forces substantially free of pressure effects, lateral deflection of the plate 14 is discussed next. The lateral deflection due to wall shear of the plate 15 may be estimated from elementary beam theory. Each support arm 16 is a clamped beam subjected to a deflection at its tip, where the plate 14 is held. Assuming that the plate 14 is rigid body, this deflection is the lateral deflection of the plate 14. From elementary beam theory, assuming no residual stress in the support arms 16, the relationship between the shearing force F and the lateral deflection $\delta$ is given by:

$$\delta = \frac{(F/2)L^3}{2EtW^3} = \frac{A_p}{4Et} \frac{L^3}{W^3} \tau. \tag{1}$$

where $A_p$ is the area of plate 14 ($=L_p^2$); $F = A_p\tau = L_p^2\tau$ is the shearing force; E is the Young's modulus of the support arm 16; and L, W, and t are the length, width, and thickness, respectively of the support arm 16. From (1) it is concluded that in order to maximize the sensitivity of sensor element 12, the support arm 16 must have a high length-to-width ratio.

On the other hand, the bandwidth of element 12 is limited by the first resonant frequency $f_1$ (for lateral motion) of the supported plate 14. An approximation of $f_1$, also assuming no residual stress in support arms 16, can be derived from Rayleigh's method where:

$$f_1 = \frac{1}{\pi}\left[\frac{t_p}{M_p} \frac{W^3}{L}\right]^{1/2} \tag{2}$$

where $M_p = \rho_p A_p t_p$ is the mass of the plate 14, $\rho_p$, $A_p$, and $t_p$ being the density, area and thickness of the plate 14. In deriving (2), the small contribution of the masses of the support arms 16 has been neglected. This result indicates that in order to maximize the bandwidth, the plate mass $M_p$ should be minimized and the support arms 16 should have a high width to length ratio in conflict with a high length to width ratio for maximizing sensitivity.

These equations must be modified if there is residual stress in the support arms 16. Equations (1) and (2) are provided as an illustration and do not represent limitation of the present invention. With or without residual stress, the bandwidth-sensitivity trade-off in the choice of the material and the length-to-width ratio for the support arms represents a fundamental design equation of the shear-sensitive plate 14.

A final consideration in analyzing the shear response is the quality factor of the lateral resonance, $Q_L$. The quality factor indicates how significant the resonant effects are to the amount of sensed shear. In order to measure the wall shear without resonant effects, the device should be operated in the stiffness regime where $f << f_1$. However, a low $Q_L$ allows the effects of the resonance, including depression of the sensitivity and excess phase shift, to be significant for frequencies much less than $f_1$. For example, if $Q_L$ is as low as 1, a substantial excess phase shift of 20 degrees may exist at frequencies less than $f_1/3$. Further, the quality of factor $Q_L$ is related to drag on the plate in the elementary analysis equation of Couette flow $$Q_L = 2\frac{d[M_p E t W^3/L^3]^{1/2}}{\mu A_p} \tag{3}$$

where $\mu$ is the absolute viscosity of air and d is the distance between the plate and the wall. From equation (3), in order to maximize $Q_L$ it is desirable to minimize the plate area $A_p$. However, $A_p$ should only be minimized to that amount which is consistent with maintaining an acceptable sensitivity given by equation (1). A similar analysis of the normal motion of the plate shows that viscous damping due to the pumping of fluid from beneath the plate results in a normal resonant effects quality factor $Q_n \approx 10^{-3}$.

Considering the design constraints of (1), (2), and (3), a range of dimensions for the micro-bridge shear stress element 12 is defined. The dimensions define a plate with a top surface area larger than any end surface area and smaller than the smallest eddy of interest. Hence, plate 14 of FIG. 2 has a thickness of about 10 microns or less and a lateral dimension on the order of about 100 to 1000 microns on a side. The small dimensions of the plate enable small eddies travelling at a fast rate to be seen over the entire surface of the plate. The plate is thus able to see such critical eddies without depending solely on its fast frequency response feature. The support arms 16 are about 10 microns wide by about 1 mm long. Further the dimensions define a cavity 21 of about less than 3 microns high such that it dampens normal movement of the plate due to air becoming viscous within cavity 21 at such dimensions. The cavity dimensions plus the plate thickness define a total height above the target wall which is small enough to not disturb the flow of the target fluid.

Such dimensions of the present invention are uncommon to prior art devices. In prior art floating element devices, a typical floating shear element is about 25 microns thick, has a surface area of about 10,000 microns by 10,000 microns and protrudes from the target wall on the order of about 25 to 50 microns. Such elements were affected only by large stresses of about 10 Pa or more. In contrast, the present invention senses shear stresses as small as about 0.4 Pa, and is highly sensitive to shear forces such that a 1 Pa shear stress on the plate results in a lateral displacement of about 0.17 μm. Also, the large suspension area of the prior art devices lead to erroneous forces due to fluid flow through the large gaps.

The next consideration is in the detection of the small lateral displacements of the shear-sensitive plate 14 due to wall shear. The element 12 of FIG. 2 uses an electronic technique based on measuring coupled capacitances that are sensitive to the motion of the shear-sensitive plate 14. Similar electronic techniques for sensing dielectric properties of materials are disclosed by S. D. Senturia in U.S. Pat. No. 4,423,371. Also, similar techniques for measuring shear in tactile sensors have been demonstrated (see "A Mutual Capacitive Normal and Shear Sensitive Tactile Sensor" by L. S. Fan, R. M. White, and R. S. Muller, IEEE International Electron Devices Meeting, San Francisco, Calif. Dec. 1984 pp. 220-222; and "Resonant-Microbridge Vapor Sensor" by Roger T. Howe and Richard S. Muller, IEEE Transactions on Electron Devices, Vol. ED-33, No. 4, April 1986).

Figure 4:
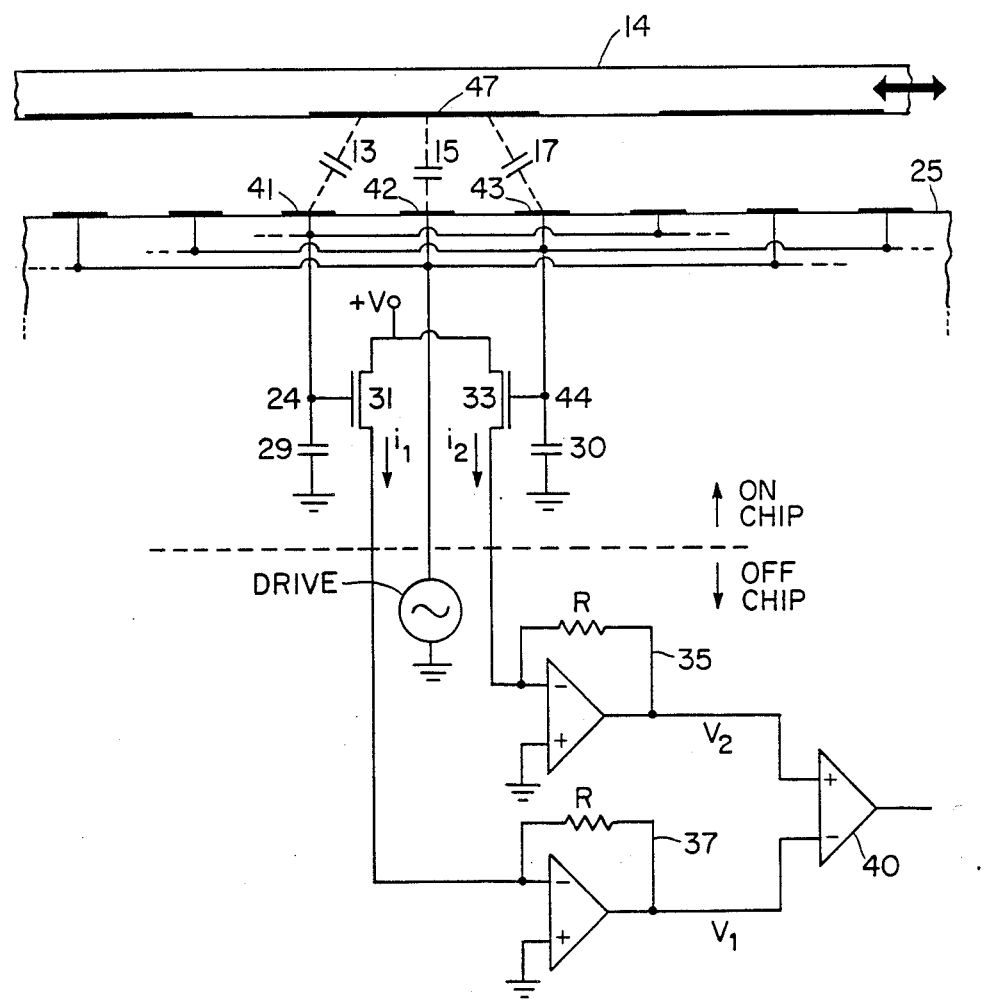
FIG. 4 is an electrical schematic diagram of an integrated capacitance-measuring circuit used as a readout scheme with the element of FIG. 1.

FIG. 4 illustrates the capacitor, electrode and circuit configuration for a very simple electronic readout scheme. The configuration uses a three-phase repeated array of electrodes 41, 42, 43. A one or more unit repeated array could also have been used. The three electrodes 41, 42, 43 are placed on the substrate 25 of FIG. 2. The electrodes are positioned beneath a conducting plate 47 which has been attached to plate 14. The conducting plate 47 can be on top of, embedded in, or beneath plate 14. The outer edges of conducting plate 47 are aligned within the bounds of the outer edges of the sensing electrodes 41 and 43. Electrode 42 is connected to an AC generator to produce a constant drive signal. Sensing electrodes 41 and 43 are capacitively coupled to drive electrode 42 via conducting plate 47 through capacitor 15, and then through respective capacitors 13 and 17. The lateral motion of plate 14 and thereby conducting plate 47 causes one of capacitors 13 and 17 to increase and the other to decrease in like amounts, and thus changes the capacitive coupling between drive and sense electrodes. The lateral deflection causes the coupling of one sense electrode 41 (or 43) to be lowered, while the coupling of the other sense electrode 43 (or 41) is increased. This change in coupling is sensed at nodes 24 and 44. With respect to the sensed increase or decrease in coupling, sensing nodes 24 and 44 place a charge from their respective capacitors 29 and 30 on the gates of respective FET's 31 and 33. The FET's should be essentially identical which is readily achieved if both are fabricated as part of the sensor using standard integrated circuit fabrication technology. In turn the FET's 31 and 33 change the current flowing to amplifier circuits 37 and 35. The change in drive of the amplifier circuits 37 and 35, provides buffered signals $V_1$ and $V_2$ which measure both magnitude and direction of the sensed wall shear. Signals $V_1$ and $V_2$ are differentially compared by differential amplifier 40 which provides an output signal indicative of the sensed wall-shear.

A readout scheme could utilize more than one set of capacitively coupled electrodes sensed by a matched air of FET's or other electronics. A separate conducting plate, a one or more unit array of electrodes and supporting electronics would be used for each set. Each set would be connected to the plate 14 and substrate 25 in a fashion similar to that described for the single readout electronics.

Figure 5:
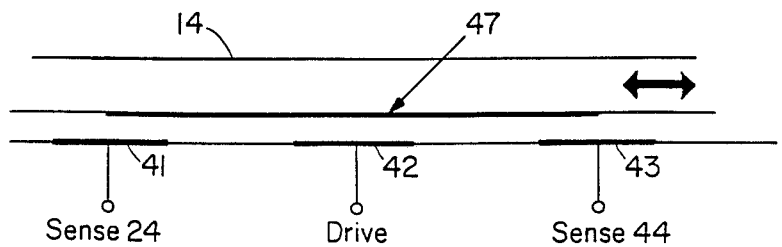
FIG. 5 is an illustration to scale of one phase of the electrode array produced by the capacitance measuring circuit of FIG. 4.

It should be pointed out that FIG. 4 is not to scale. FIG. 5 illustrates one phase of the electrode array to scale. This cross section highlights two important points regarding this detection scheme: (1) the change in coupling capacitance will be linear in $\tau$ to first order, by design, and (2) any normal displacement of the plate will affect all three capacitors 13, 15, and 17 by the same proportion so that the relative coupling between drive and sense electrodes is not affected, and further affects the coupling capacitors 13 and 17 equally allowing for the elimination of normal response by subtracting the two sense signals. Alternatively, a measurement of current $i_1$ in one side (or $i_2$ in the other side) can be obtained by use of an ammeter or other current measuring means. The current measurement serves as a measurement of normal displacement. According to the previous discussion, pressure fluctuations will not cause significant normal displacements of the shear-sensitive plate 14. However, it is possible that vibration of the target wall could couple into the very heavily damped normal mode of the microstructure. Hence, this electronic cancellation of the effects of potentially disruptive normal motion has utility.

We next consider the performance of this readout circuit of FIG. 4 for the embodiment having plate 14 whose dimensions are as previously stated. Using about 5 μm wide sense electrodes 41, 42, and 43 and assuming that a 1% capacitance difference is the circuit resolution, a lateral displacement of 0.05 μm can be detected. Given the sensitivity of 0.17 μm/Pa by design, this estimate corresponds to a minimum detectable shear of about 300 to 400 mPa. For a typical value $\tau_{rms} = 1$ Pa, this result indicates that this embodiment of the microsensor has a 60 dB signal-to-noise ratio.

The method described above is very attractive as a first generation embodiment because of the relative ease of fabrication of the metal-gate field-effect transistors and its compatibility with the shear-sensitive plate process. A second generation embodiment would more likely include CMOS integrated detection electronics as well as analog-to-digital conversion to facilitate data acquisition from arrays of shear-sensitive elements. On such promising approach under investigation at MIT is based on a switched-capacitor (charge redistribution) CMOS analog-to-digital converter. Other structures embodying the present invention include a circular plate with support arms which levitate the plate and allow rotation of the plate. This rotor embodiment would provide a measurement of the rotational forces acting on the plate or the ability of the plate to rotate.

Figure 6:
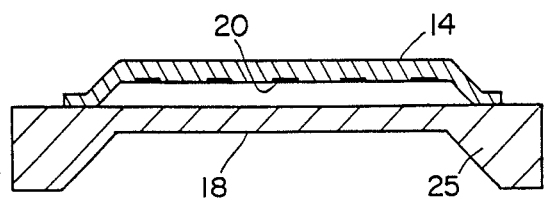
FIGS. 6 and 7 are schematic views of embodiments of the invention with optical readout means.

Other embodiments would include optical devices for detection and measurement of the lateral displacement of plate 14. Such devices would include microscopes, fiber optics and pattern differentiation means. FIG. 6 illustrates one such pattern differentiation device. The device includes a pattern 20 structured in plate 14 such that the pattern provides a distinguishing optical feature. This pattern 20 is visible and viewed through a silicon nitride window 18 which is conventionally fabricated in the substrate 25. A window made by other means is also suitable.

Figure 7:
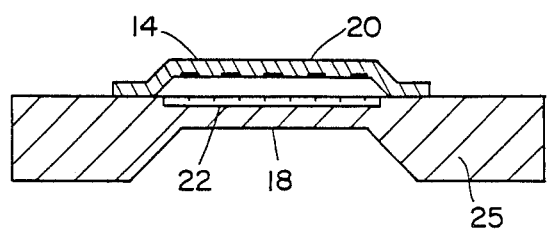

In a second optical embodiment shown in FIG. 7, optical scale 22 is patterned within substrate 25. Plate pattern 20 is measured against optical scale 22. When plate 14 is deflected, the plate pattern 20 will be misaligned with the substrate scale 22. This misalignment can be viewed by shining a light through the substrate window 18 such that reflections are obtained form the optical distinguishing features 20 of plate 14. The reflections are then measured against the substrate pattern scale 22. With proper calibration of the substrate scale 22, an indication of the deflection and shear stress can be calculated from the measured amount of misalignment.

While various readout schemes may be employed, the structure of the microbridge remains largely unchanged. Fabrication of the microbridge with the capacitance readout scheme is described next. However, it is understood that the general microstructure may be fabricated by a similar process and the other readout schemes readily incorporated. The plate 14 with electronic readout is fabricated by first using conventional integrated-circuit processing to make the readout electronics and then by employing surface micromachining technology to make the bridge plate 14. No innovations or changes need be made in the electronic fabrication since the shear-sensitive element process utilizes conventional electronic materials and low processing temperatures.

Figure 8:
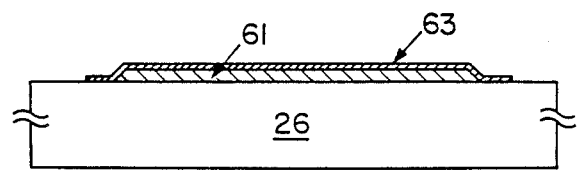
FIG. 8 is an illustration of the surface micromachining process for fabricating a sensor embodying the present invention.
Figure 8:
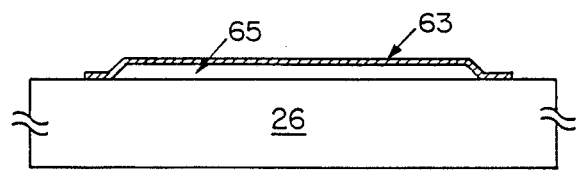

The basic surface micromachining process in which the plate and arms are monolithically fabricated is illustrated in FIG. 8. Integrated-circuit processing techniques are used to deposit and pattern two thin films 61 and 63 onto the silicon substrate 26. The sacrificial film 61 is patterned by photolithography techniques onto substrate 26 and comprises soft metal such as nickel or aluminum. The structural film 63 is deposited and patterned over the sacrificial film 61. The structural film 63 may comprise a polymer for necessary lateral stiffness in the structure. It is film 63 that actually forms the supporting arms 16 of FIG. 1, bases 19 connecting the arms 16 to the substrate 26, and shear-sensitive plate 14 itself. The thin-film sandwich of films 61 and 63 is then exposed to a selective etchant that removes the lower, sacrificial layer 61, leaving the upper layer 63, and thus, plate 14, suspended above the substrate 26. A gap 65 is formed where the sacrificial layer 61 has been selectively etched. Gap 65 has dimensions defined by the sacrificial layer 61 as deposited before the etching.

The structure illustrated in FIG. 8, is a homogeneous layer; however, the interdigitated electrodes needed for the capacitive readout are readily incorporated into substrate 26 and standing microstructure 63. The electrode metallization need only resist the etchant used to remove the sacrificial layer 61. Polyimide, a high-temperature electronic polymer, is one such structural film for microsensor applications. After the sacrificial layer 61 is deposited on substrate 26, a layer of the polymer may be deposited. The conducting layer forming conducting plate 47 may be deposited between 2 coats of the polymer, on top of or below the polymer such that conducting plate 47 is embedded in, on top of, or beneath plate 14. The electrodes 41, 42, 43 are diffused or deposited into substrate 26. They are separated from plate 14 by sacrificial layer 61.

It is in or just below the structural film that optical distinguishing features may be placed for optical readout schemes. After etching, a silicon nitride layer is deposited on the substrate and provides the window. The substrate is then cut or etched to provide a view of the microbridge plate 14 through the silicon nitride window.

Figure 9:
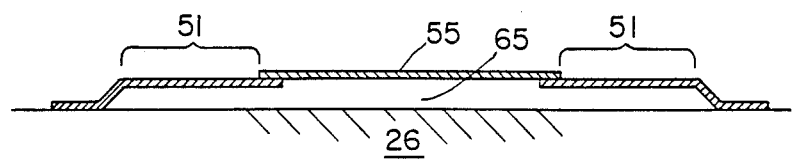
FIG. 9 is a cross section of a microbridge element of the present invention having a plate comprising different material than the arms.

For mechanical stability of plate 14, it is desirable that the thin-film plate behave as a rigid body. This objective is accomplished in a modified structure shown in FIG. 9. This structure utilizes an inorganic thin film of high Young's modulus for the plate 55, such as silicon nitride, and polyimide for the support arms 51. To avoid affecting the transistor structures of the capacitor readout scheme, the nitride film must be deposited by a low temperature technique, such as sputtering or plasma-enhanced chemical vapor deposition. The plate material must also have low internal stress and exhibit good adhesion with respect to the electrode metallization and polyimide support arms 51.

Figure 10:
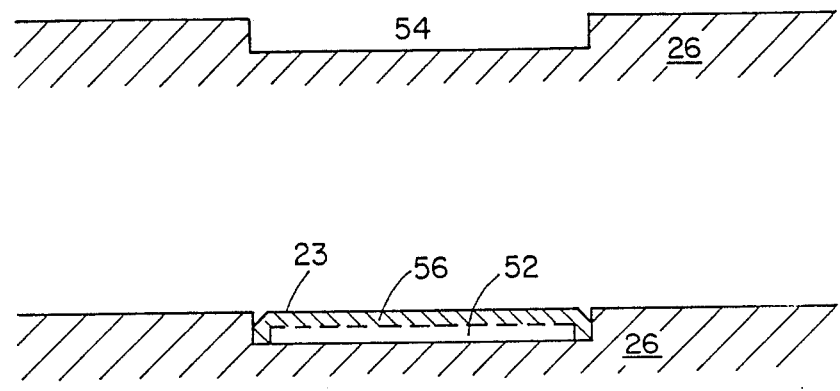
FIG. 10 is an illustration of another surface micromachining process for fabricating an inlaid sensor embodying the present invention.

As shown in FIG. 10, the microbridge may as be fabricated so that the top surface 23 of the microbridge sensor is smooth with the substrate. This arrangement involves etching a recess or pit 54 into the substrate 26. A sacrificial layer 52 is then deposited into the pit 54. The structural layer 56 is patterned and deposited over the sacrificial layer 52. The sacrificial layer 52 is removed by etching and forms a cavity in its place. The remaining structure is a microbridge which is flush with the surface of the substrate 26 and behaves like the microbridge previously described. Like the fabrication of the microbridge of FIG. 2, this fabrication technique can incorporate the integrated circuitry or other elements of the other readout schemes.

Figure 11A:
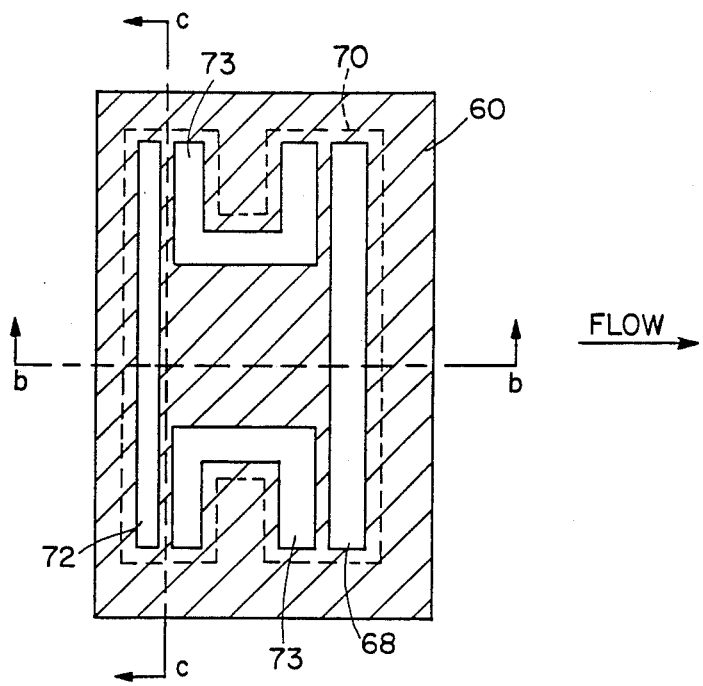
FIG. 11a is a plan view of another microbridge shear-sensitive element with a limited cavity embodying the present invention.
Figure 11B:
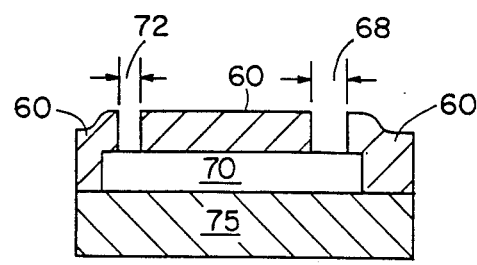
FIG. 11b is a cross section of the element in FIG. 11a through line b—b.
Figure 11C:
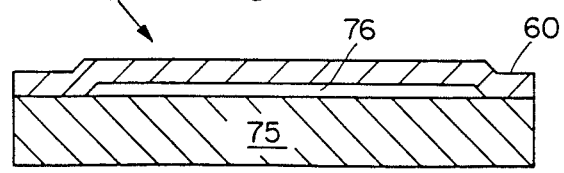
FIG. 11c is a cross section of the element in FIG. 11a through line c—c.

As shown in FIG. 11, the microbridge may also be fabricated so that the structural film 60 covers the whole wafer 75. In this fabrication process the structural film 60 is deposited and patterned over the sacrificial film 70 and over the exposed surface of the wafer 75 leaving two gaps 72 and 68 and two additional spaces 73, as shown in FIG. 11a. Gap 68 and 72 and spaces 73 allow exposure of sacrificial layer 70. Gap 68 is formed on the side of the microbridge which receives the flowing fluid after gap 72, and gap 68 is wide enough to permit lateral motion of the plate in the flowing fluid. Suitable gap width dimensions for gap 68 are in the range of about 5–50 $\mu$m. Gap 72 is not restricted in width by the lateral plate motion; a suitable width for gap 72 is about 5 $\mu$m. The portions of spaces 73 opposite to gap 72 must, like gap 68, be wide enough to permit lateral motion of the plate. The structural film directly covering the wafer is planarized to a thickness which is greater than the height of cavity 76 as shown in FIG. 11b and 11c. This provides for minimal vertical protuberation of the microbridge 79 from the target floor.

Figure 12A:
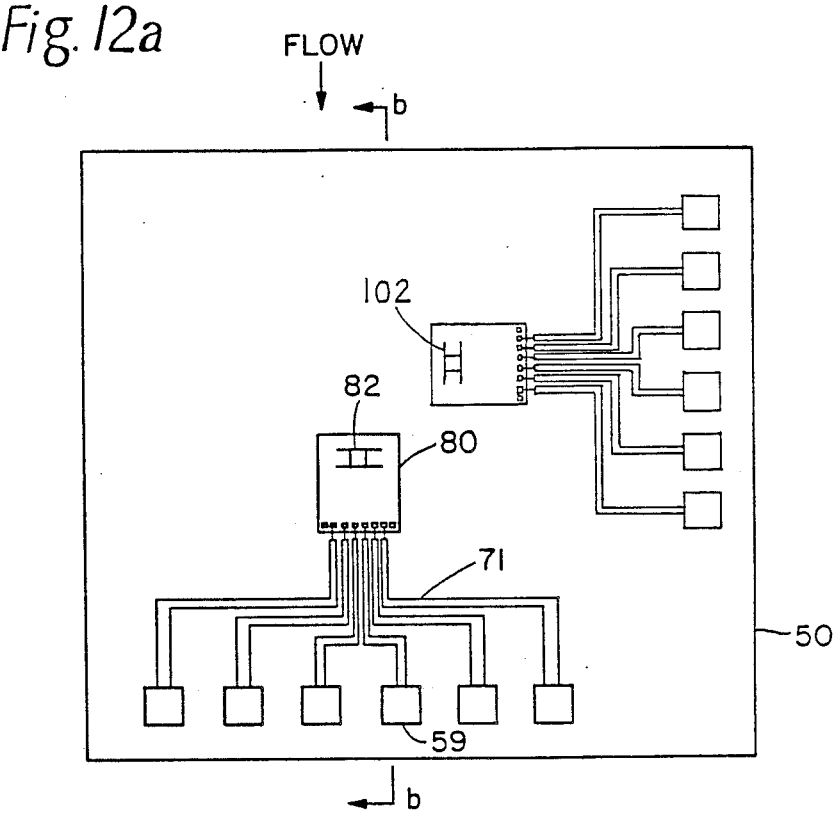
FIG. 12a is a plan view of a holding plate for placing a sensor embodying the invention in a target wall.
Figure 12C:
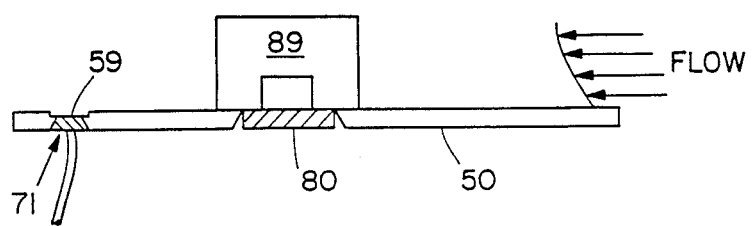
FIG. 12c is a cross section of the holding plate with a jig pressing piece aligning the sensor member with the holding plate.
Figure 12B:
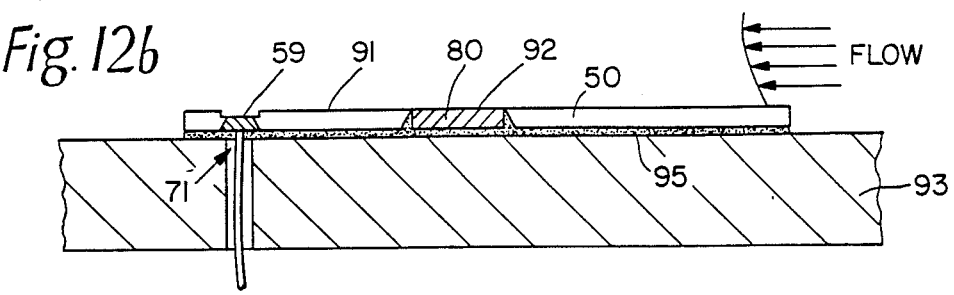
FIG. 12b is a cross section of the holding plate of FIG. 12a through line b—b placed in a support piece.

The microbridge sensor may be placed in the target area by several schemes. FIGS. 12a and 12b show one method of placement which includes a macro-support structure. The wafer 80, as shown in FIG. 12a, is the wafer in which the microbridge element 82 is fabricated. The wafer 80 is fitted into a hole cut or etched into silicon holding plate 50. The hole is the same size as the microbridge wafer 80 so that the wafer perfectly fits into the hole. The top surface 92 of wafer 80 is aligned flush with top surface 91 of holding plate 50. Any connections to readout electronics involved are threaded through holes 59 in the holding plate 50 on the side of the microbridge opposite of the flow so as to not disturb the flow before sensing it. Several microbridge wafers such as that of microbridge element 102 in FIG. 12a, may be similarly packed into holding plate 50 which covers a large surface area in the target wall relative to the size of the microbridge. Holding plate 50 fits into a matching slot in the macro-support structure 93 in the target wall and is adhered in place by an epoxy 95. The subject flow is undisturbed by the structure which is flush with the surface of the target wall.

The microbridge sensor may be aligned flush with the macro-support structure by several schemes. One such surface alignment means is a jig piece 89 shown in FIG. 12c. Jig piece 89 presses the microbridge silicon wafer 80 and a silicon holding plate 50 into the common macro-support structure 93 so that the top surface 92 of wafer 80 is within about 1 micron of surface 91 of holding plate 50. The holding plate 50 with wafer 80 fits into the matching slot in the common macro-support 93 and is adhered in place by an epoxy 95. After the epoxy is set, the jig piece 89 is removed leaving the surfaces of holding plate 50 and wafer 80 aligned with each other and flush with the target wall.

The foregoing microstructure used as a shear stress sensor may also be used to measure acceleration. The force, F, due to acceleration will be $$F = Ma$$

where M is the mass of the plate member and a is the acceleration. For the case of a plate member 14 of a microstructure 12 embodying the present invention as shown in FIGS. 13a-13c, the mass is $$M = \rho t WL$$

where $\rho$ is the density of the material used to fabricate the plate member 14 (polyimide), t is the thickness of the plate member 14, and W and L are the width and length respectively. If force F in the foregoing equation is normalized by the surface area of the plate member. WL, an effective shear stress for the structure 12 is defined as $$\tau_{eff} = \frac{\rho t W L a}{WL} = \rho t a$$

For an acceleration of gravity (9.8 m/s$^2$), a plate member thickness of 30 $\mu$m and using the density of polyimide (1400 kg/m$^3$), the effective shear stress is 0.42 Pa. The shear stress sensor has been demonstrated in a previous discussion to detect shear stresses of the order of 1 Pa, and thus the microstructure 12 shown in FIGS. 13a-13c has acceleration sensitivity of at least 1 g.

FIG. 14 shows the result of an experiment to measure acceleration sensitivity. The microstructure 12 (micron sized accelerometer) is rotated 180° through its sensitive axis (the axis along which length L is measured) and the output voltage of the differential circuit is plotted as shown in FIG. 14.

The principle advantage of the structure of FIGS. 13a-13c over other microfabricated accelerometers is its compatability with standard integrated circuit processing. This advantage comes about because the mechanical structure is fabricated using low temperature processes after the integrated electronics have been fabricated as described in FIG. 8. Thus, there is very little difficulty in merging the mechanical structure fabrication process with a standard IC process. In addition, the process for making the mechanical structure employs standard process sequences. There is no need for non-standard anisotropic etching technologies which are commonly used in making microfabricated accelerometers. This is an advantage both in ease of fabrication and in reduced die size. Furthermore, the mechanical element fabrication requires only three photolithographic mask steps after the electronics have been fabricated. Finally, the simplicity of the fabrication along with its process compatability and reduced size suggests that a part such as this could be fabricated and packaged at very low cost.

The microstructure employed for measuring shear stress is enhanced for purposes of measuring acceleration as follows. Geometries of the arms 16 are designed such that the microstructure is sensitive to acceleration in two dimensions in the plane of the wafer 25 as shown in FIG. 13a. Also, if the wafer is packaged in a vacuum, it will be possible to obtain dynamic response to geometrically normal forces because of the elimination of viscous damping within the cavity 21 beneath the plate member 14. In this way it is possible to build an accelerometer on a chip for detecting acceleration along three orthogonal axes.

Given the compatability with the readout electronics processes, more analog circuitry can be included on the chip to improve sensitivity. Also the design of the structure may be tailored in order to design structures with different acceleration ranges and sensitivities.

While the invention has been particularly shown and described with reference to the preferred embodiments thereof, it will be understood by those who are skilled in the art that there are changes in form and detail that may be made without departing from the spirit and scope of the invention as defined by the appended claims. For example, although the embodiment disclosed herein detects shear in one direction, another embodiment to detect orthogonal shear stresses with a second or more sensors such as sensor 102 shown in FIG. 12a is possible.

We claim:

1. A wall shear stress microsensor comprising:
   a microndiminsioned shear-sensitive plate;
   a plurality of supporting arms which suspend the plate above a substrate and define a cavity between the plate and the substrate, the cavity being so small that it dampens movement of the plate normal to the plane of the plate through viscous forces generated within the cavity; and
   readout means for providing an indication of the deflection of the plate and thereby a measurement of the shear stress of interest.

2. A wall shear stress microsensor as claimed in Claim 1 wherein the microdimensions of the plate cause environmental pressures to be uniformly felt throughout an entire top surface of the plate such that the plate in combination with the damping effect of the cavity renders the sensor substantially insensitive to pressures, and shear lateral forces are sensed substantially independent of pressure.

3. A wall shear stress microsensor as claimed in claim 2 wherein the microdimensions of the plate include a top surface area which is greater than an end surface area lying in a plane perpendicular to the plane in which the top surface area lies, and said top surface area is an order of magnitude smaller than an area in which the smallest eddy of interest is uniform.

4. A wall shear stress microsensor as claimed in claim 2 wherein the microdimensions of the plate include a dimension along a length of the top surface no bigger than about 5L* to about 10L* and a total height or protrusion above a target surface no higher than about 2L* to about 3L* where L* is a relevant length scale in turbulent flow such that $$L^* = \nu/u^*$$

where $\nu$ is a kinematic viscosity equal to $\mu/\rho$ and u* is friction velocity equal to $$\sqrt{\frac{\tau}{\rho}}.$$

where $\mu$ is absolute viscosity of the target fluid, $\rho$ is density and $\tau$ is shear stress.

5. A wall shear stress microsensor as claimed in claim 2 wherein the plate has a lateral dimension along a length of its top surface of about 1000 microns or less and is suspended about 10 microns or less above the substrate.

6. A wall shear stress microsensor as claimed in claim 5 wherein a longitudinal dimension of the cavity between the plate and substrate is less than a longitudinal dimension of the supporting arms between the substrate and a top surface of the supporting arms.

7. A wall shear stress microsensor as claimed in claim 1 wherein the readout means for providing an indication of the deflection of the plate and measurement of the shear stress includes an integrated differential capacitance circuit.

8. A wall shear stress microsensor as claimed in claim 7 wherein the integrated differential capacitance circuit comprises:
 a conducting layer attached to the plate;
 three conductors attached to the substrate, two positioned to the outside of the third, the third conductor being in the middle, the conducting layer of the plate being aligned within the two outer positioned substrate conductors, the conducting layer being capacitively coupled with the conductors attached to the substrate; and
 means for sensing a change in capacitive coupling between the conductive layer and the outer positioned substrate conductors where lateral motion of the plate changes the capacitive coupling between the conducting layer and the outer positioned substrate conductors, one outer positioned substrate conductor experiencing a lowered coupling, the other outer positioned substrate conductor experiencing an increased coupling, said sensing means sensing the change in coupling and producing a signal indicative of the deflection of the plate and thereby sensed shear stress.

9. A wall shear stress microsensor as claimed in claim 8 wherein the means for sensing a change in capacitive coupling includes:
 two sensing nodes, one for each outer positioned substrate conductor, each sensing node sensing the change in coupling experienced by its respective substrate conductor; and
 two field effect transistors (FET's) one for each sensing node, where each sensing node senses a change in coupling of its respective outer positioned substrate conductor and places charge on its respective FET, the FET's connected to a differential amplifier circuit which is sensitive to the difference in current from the two FET's and therefrom provides an output signal indicative of the sensed wall shear.

10. A wall shear stress microsensor as claimed in claim 9 wherein the two FET's are essentially the same.

11. A wall shear stress microsensor as claimed in claim 9 wherein the differential amplifier circuit is off chip and comprises two amplifiers, one connected to one FET, the second connected to the other FET, the FET's changing current flow to each respective amplifier such that said amplifiers produce signals which are differentially compared to provide an output signal indicative of sensed wall shear.

12. A wall shear stress microsensor as claimed in claim 8 wherein said circuit is integrated into the microsensor by micro-fabrication of films on the substrate by the process of:
 depositing a sacrificial film on the substrate, the substrate fabricated with the conductors of the integrated circuit;
 depositing a second film onto the sacrificial film such that said second film is connected to the conducting layer and patterned to form the plate and supporting arms; and
 removing only the sacrificial film leaving the plate defined by the second film connected to the conducting layer and suspended above the substrate by the supporting arms, and leaving the conductors connected to the substrate.

13. A wall shear stress microsensor as claimed in claim 8 wherein an array of shear-sensitive plates with said support arms and said integrated differential capacitance circuits is repeated on one substrate to provide multi-point measurements.

14. A wall shear stress microsensor as claimed in claim 1 wherein the readout means includes optical readout means.

15. A wall shear stress microsensor as claimed in claim 14 wherein said optical readout means include:
 a window in the substrate;
 a distinguishing optical feature associated with the plate and open to the window; where the distinguishing optical feature moves with the plate and is viewed through the window to provide an indication of the amount of plate deflection and thereby shear stress.

16. A wall shear stress microsensor as claimed in claim 15 wherein said optical readout means further include an optical scale associated with the window, said scale enabling a user to measure the amount of deflection of the plate and thereby shear stress by viewing through the window the change in position of the optical distinguishing feature of the plate relative to said scale where the optical distinguishing feature moves with the plate and the scale remains relatively stationary.

17. A wall shear stress microsensor as claimed in claim 1 wherein the plate is suspended within a recess in the substrate and the cavity is formed between the plate and base of the recess.

18. A wall shear stress microsensor as claimed in claim 17 wherein the plate has a lateral top surface which is flush with the surface of the substrate, said plate top surface being open to the turbulent flow creating the shear stress of interest.

19. A wall shear stress microsensor as claimed in claim 18 wherein said plate has lateral dimension along a length of the top surface which is n order of magnitude smaller than a length dimension of the smallest eddy of interest.

20. A wall shear stress microsensor as claimed in claim 18 wherein the microdimensions of the plate include a length dimension no bigger than about 5L* to about 10L* and a total height or protrusion above a target surface no higher than about 2L* to about 3L* where L* is a relevant length scale in turbulent flow such that $$L^* = \frac{\nu}{u^*}$$

where $\nu$ is kinematic viscosity equal to $\mu/\rho$ and u* is friction velocity equal to $$\sqrt{\frac{\tau}{\rho}},$$

where $\mu$ is absolute viscosity of the target fluid, $\rho$ is density and $\tau$ is shear stress.

21. A wall shear stress microsensor as claimed in claim 18 wherein said plate has a lateral dimension along a length of its top surface of less than about 1000 microns and the cavity is less than about 10 microns in height between the plate and base of the recess.

22. A wall shear stress microsensor as claimed in claim 17 wherein the readout means includes an integrated differential capacitance circuit.

23. A wall shear stress microsensor as claimed in claim 22 wherein the integrated differential capacitance circuit comprises:
a conducting layer connected to the plate;
three conductors connected to the substrate, two of the three conductors positioned on the outside of the third, the third being in the middle, said conducting layer of the plate being aligned within the two outer positioned substrate conductors, the conducting layer being capacitively coupled with the conductors connected to the substrate; and
means for sensing a change in capacitive coupling between the conducting layer and the two outer positioned substrate conductors where lateral motion of the plate changes the capacitive coupling between the conducting layer and the outer positioned substrate conductors, one outer positioned substrate conductor experiencing a lowered coupling, the other outer positioned substrate conductor experiencing an increased coupling, said sensing means sensing the change in coupling and producing a signal indicative of the deflection of the plate and thereby sensed shear stress.

24. A wall shear stress microsensor as claimed in claim 23 wherein the means for sensing a change in capacitive coupling includes:
two sensing nodes, one for each outer positioned substrate conductor, each sensing node sensing the change in coupling experienced by its respective substrate conductor;
two field effect transistors (FET's) one for each sensing node where each sensing node senses a change in coupling of its respective outer positioned substrate conductor and places charge on its respective FET, the FET's connected to a differential amplifier circuit which is sensitive to the difference in current flowing from the two FET's and therefrom provides an output signal indicative of the sensed wall shear.

25. A wall shear stress microsensor as claimed in claim 24 wherein the two FET's are substantially the same.

26. A wall shear stress microsensor as claimed in claim 24 wherein the differential amplifier circuit is off-chip and comprises two amplifiers, one connected to one FET, the second connected to the other FET, the FET's changing current flow to their respective amplifier such that said amplifiers produce signals which are differentially compared to provide an output signal indicative of sensed wall shear.

27. A wall shear stress microsensor as claimed in claim 23 wherein said circuit is integrated into the microprocessor by microfabrication of films in the recess of the substrate by the process of:
depositing a sacrificial film in the substrate recess, the base of the recess fabricated with the three conductors of the circuit;
depositing a second film over the sacrificial film such that said second film is connected to the conducting layer and is patterned to form the plate and supporting arms; and
removing only the sacrificial film and
leaving the plate defined by the second film connected to the conducting layer and suspended within the recess by the support arms, and the conductors connected to the base of the recess.

28. A wall shear stress microsensor as claimed in claim 22 wherein an array of shear-sensitive plates with said arms and said integrated differential capacitance circuits is repeated on one substrate to provide multiple point measurements.

29. A wall shear stress microsensor as claimed in claim 17 wherein the readout means includes optical readout means.

30. A wall shear stress microsensor as claimed in claim 29 wherein said optical readout means include:
a window in the base of the recess; and
a distinguishing optical feature on the plate open to the window where the distinguishing optical feature moves with the plate and is viewed through the window to provide an indication of the amount of plate deflection and thereby the amount of detected shear stress.

31. A wall shear stress microsensor as claimed in claim 30 wherein said optical readout means further include an optical scale associated with the window, said scale enabling a measurement of the amount of deflection of the plate and thereby shear stress to be obtained by viewing through the window the change in position of the distinguishing optical feature of the plate relative to said scale where the distinguishing optical feature moves with the plate and the scale remains relatively stationary.

32. A wall shear stress microsensor as claimed in claim 1 further comprising mounting means to position said shear-sensitive plate, arms and readout means in a target flow substantially flush with a target wall such that said target flow is not disturbed by said plate, arms and readout means.

33. A wall shear stress microsensor as claimed in claim 32 wherein said mounting means includes a holding plate into which are evenly and smoothly fitted one or more substrates on which the shear-sensitive plate, arms and readout means are fabricated, where said holding plate fits into a matching slot and is adhered in place in a support structure in the target wall which covers a large surface area of the target wall compared to the size of a substrate and which is smooth with the target wall.

34. A sheer stress sensor having a bridge shape of microndimensions which render it substantially insensitive to pressure and sensitive to lateral forces independent of pressure, by the microndimensions causing the effects of pressure to be uniform throughout both an entire top surface and a bottom surface of the sensor and the microndimensions defining a passageway under the sensor so small that a damping effect of geometrically normal movement of the sensor under effects of vibrational forces is produced by a viscous drag within that passageway.

35. A shear stress sensor as claimed in claim 34 wherein the microdimensions are an order of magnitude less than dimensions of the smallest eddies of interest.

36. A shear stress sensor as claimed in claim 34 wherein the microdimensions include a dimension along a length of the top surface no larger than about 5L* to about 10L* and protrusion above a target surface no more than about 2L* to about 3L* where L* is a relevant length scale in turbulent flow defined by $$L^* = v/u^*$$

where $v$ is kinematic viscosity equal to $\mu/\rho$ and u* is frictional velocity equal to $$\sqrt{\frac{\tau}{\rho}},$$

where $\mu$ is absolute viscosity of the target fluid, $\rho$ is density and $\tau$ is shear stress.

37. A shear stress sensor as claimed in claim 34 wherein said dimensions include: a dimension along a length of the top surface less that about 1000 microns, and a height under the sensor of less than about 10 microns.

38. A shear stress sensor as claimed in claim 34 wherein said microndimensions are generated by microfabrication of two films on a substrate by the process of:
   depositing a sacrificial film on the substrate;
   depositing onto the sacrificial film a second film and patterning said second film to form a microndimensioned top surface; and
   removing the sacrificial film leaving the microdimensioned top surface defined by the second film suspended above the substrate at the very small height and leaving a cavity where the sacrificial film was previously deposited.

39. A shear stress sensor as claimed in claim 38 wherein said second film is further deposited over the whole surface of the substrate leaving an undeposited area for access to the sacrificial film on one side of the defined top surface and leaving another area for allowance for lateral deflection on an opposite side of the top surface, said further deposited second film being made to a thickness which is greater than the height under the sensor.

40. A bridge-shaped structure having a top surface exposed to environmental effects and an opposite surface facing a plane on which legs of the bridge structure stand, the bridge structure being of micron dimensions which render it substantially insensitive to pressure and sensitive to lateral forces independent of pressure, by the micron dimensions causing the effects of pressure to be uniform throughout the entire top surface of the bridge-shaped structure and the micron dimensions defining a space between the opposite surface and the plane under the bridge structure so small that a damping effect of normal movement of the bridge-shaped structure is produced by a viscous drag within the space.

41. A bridge structure as claimed in Claim 40 wherein the micron dimensions are an order of magnitude less than smallest eddies to which the bridge structure is exposed.

42. A bridge structure as claimed in claim 40 wherein the micron dimensions include a lateral dimension of the top surface no larger than about 5L* to about 10L* and a protrusion above a target surface no more than about 2L* to about 3L* where L* is a relevant length scale in turbulent flow defined by $$L^* = v/u^*$$

where $v$ is kinematic viscosity equal to $\mu/\rho$ and u* is friction velocity equal to $$\sqrt{\frac{\tau}{\rho}},$$

where $\mu$ is absolute viscosity of the target fluid, $\rho$ is density and $\tau$ is shear stress.

43. A bridge structure as claimed in claim 40 wherein said dimensions include:
   a top surface lateral dimension less than about 1000 microns and a height under the bridge structure of less than about 10 microns.

44. A bridge structure as claimed in claim 40 wherein said micron dimensions are generated by microfabrication of two films on a substrate by the process of:
   depositing a sacrificial film on the substrate;
   depositing onto the sacrificial film a second film and patterning and said film to form a micron dimensioned top surface; and
   removing the sacrificial film leaving the micron dimensioned top surface defined by the second film suspended above the substrate at the very small height and leaving a cavity where the sacrificial film was previously deposited.

45. A bridge structure as claimed in claim 44 wherein said second film is further deposited over the whole surface of the substrate leaving an undeposited area for access to the sacrificial film on one side of the defined top surface and leaving another area for allowance for lateral deflection on an opposite side of the top surface, said further deposited second film being made to a thickness which is greater than the height under the bridge structure.

46. A micron dimensioned sensor for sensing lateral movement, the sensor comprising:
   a micron dimensioned plate;
   a plurality of supporting arms which suspend the plate above a substrate and define a cavity between the plate and the substrate, such that the plate is sensitive to lateral forces independent of pressure by the cavity being so small that it dampens movement of the plate normal to the plane of the plate through viscous forces generated within the cavity; and
   means for providing an indication of deflection of the plate and thereby a measurement of lateral movement.

47. A micron dimensioned sensor as claimed in claim 46 wherein the micron dimensions of the plate cause environmental pressures to be uniformly felt throughout an entire top surface of the plate such that the plate in combination with the damping effect of the cavity renders the sensor substantially insensitive to pressures, and lateral forces are sensed substantially independent of pressure.

48. A micron dimensioned sensor as claimed in claim 46 wherein the micron dimensions of the plate include a top surface area which is greater than an end surface area lying in a plane perpendicular to the plane in which the top surface area lies, and said top surface area if an order of magnitude smaller than an area in which the smallest eddy of interest is uniform.

49. A micron dimensioned sensor as claimed in claim 46 wherein the plate has a lateral dimension along a length of its top surface of about 1000 microns or less and is suspended about 10 microns or less above the substrate.

50. A micron dimensioned sensor as claimed in claim 46 wherein the means for providing an indicating of deflection provides a measurement of acceleration.

51. A shear stress microsensor comprising:
a plate having one surface open to shear force of interest and a surface opposite the one surface, the one surface having a lateral dimension of less than about 1000 microns such that the smallest eddies of interest are uniformly felt across the one surface of the plate;
four microndimensioned support arms, one end of each arm connected to the plate, an opposite end of each arm connected to a substrate such that said arms suspend the plate above the substrate at a height of less than about 10 microns with said plate surface opposite the one surface facing the substrate where a cavity is formed there between, the cavity dampening movement of the plate normal to the substrate by generating a viscous drug;
a conducting layer connected to the plate and capacitively coupled with three conductors attached to the substrate, two conductors positioned one on one side of the third conductor and the second on an opposite side of the third conductor, the third conductor connected to generator means, the conducting layer aligned between longitudinal axes along which the two conductors are respectively positioned on the opposite sides of the third conductor; and
means for sensing a change in capacitive coupling of the conducting layer and the three conductors, said change in coupling being indicative of lateral deflection of the plate and thereby sensed shear stress, the lateral deflection being detected substantially independent of pressure affects and movement of the plate normal to the substrate.

52. A shear-stress microsensor as claimed in claim 51 wherein said means for sensing a change in capacitive coupling includes to matching on-chip field effect transistors, one transistor coupled to a first sensing node for sensing change in capacitive coupling of the conducting layer and one conductor, the second transistor coupled to a second sensing node for sensing change in capacitive coupling of the conducting layer and another conductor.

53. A shear-stress microsensor as claimed in claim 51 further comprising mounting means to position said plate, arms and means for sensing a change in capacitive coupling, in a target flow substantially flush with a target wall such that said target flow is not disturbed by said plate, arms and readout means.

54. A shear-stress microsensor as claimed in claim 53 wherein said mounting means includes a holding plate into which are perfectly fitted one or more wafers on which the plate, arms and sensing means are fabricated, where said holding plate fits into a matching slot and is adhered in place in a support structure in the target wall which covers a large surface area of the target wall compared to the size of a wafer and which is smooth with the target wall.

* * * * *

UNITED STATES PATENT AND TRADEMARK OFFICE
CERTIFICATE OF CORRECTION

PATENT NO. : 4,896,098

DATED : January 23, 1990

INVENTOR(S) : Joseph H. Haritonidix, Roger T. Howe, Martin A. Schmidt and Stephen D. Senturia It is certified that error appears in the above-identified patent and that said Letters Patent is hereby corrected as shown below:

Claim 48, line 5, delete "if", and insert ---is---.

Signed and Sealed this

Eighteenth Day of December, 1990

Attest:

HARRY F. MANBECK, JR.

Attesting Officer

Commissioner of Patents and Trademarks